United States Patent
Cerasoli

(10) Patent No.: US 7,806,851 B2
(45) Date of Patent: Oct. 5, 2010

(54) APPARATUS FOR APPLYING AND REMOVING CLOSING MEANS FROM AN END PORTION OF A TUBULAR ELEMENT AND THE USE THEREOF IN PERITONEAL DIALYSIS

(75) Inventor: Paolo Cerasoli, San Giovanni Teatino (IT)

(73) Assignee: Glomeria Therapeutics, San Giovanni Teatino (CH) (IT)

( * ) Notice: Subject to any disclaimer, the term of this patent is extended or adjusted under 35 U.S.C. 154(b) by 463 days.

(21) Appl. No.: 10/586,495

(22) PCT Filed: Feb. 23, 2005

(86) PCT No.: PCT/IT2005/000098

§ 371 (c)(1),
(2), (4) Date: Aug. 14, 2006

(87) PCT Pub. No.: WO2005/082437

PCT Pub. Date: Sep. 9, 2005

(65) Prior Publication Data

US 2007/0161946 A1  Jul. 12, 2007

(30) Foreign Application Priority Data

Feb. 27, 2004 (IT) .......................... PE04A000004
Aug. 11, 2004 (IT) .......................... PE04A000016

(51) Int. Cl.
*A61M 1/00* (2006.01)

(52) U.S. Cl. ............................ 604/29; 604/32; 604/248; 604/535; 604/537; 137/625.46

(58) Field of Classification Search .................. 604/28, 604/29, 32, 33, 246, 248, 249, 533–539, 604/905; 137/625.46, 625.47, 625.48, 625.49, 137/625.5, 625.11, 625.14, 625.15; 251/304
See application file for complete search history.

(56) References Cited

U.S. PATENT DOCUMENTS

| 2,838,270 | A | * | 6/1958 | Danielson ..................... 251/110 |
| 3,157,201 | A | * | 11/1964 | Littmann ................. 137/625.47 |
| 3,508,582 | A | * | 4/1970 | Aulisa ..................... 137/625.11 |
| 3,957,082 | A | * | 5/1976 | Fuson et al. ........... 137/625.41 |
| 4,412,834 | A | * | 11/1983 | Kulin et al. ..................... 604/29 |
| 4,581,014 | A | * | 4/1986 | Millerd et al. ................. 604/80 |
| 4,604,093 | A | * | 8/1986 | Brown et al. |
| 4,738,668 | A | * | 4/1988 | Bellotti et al. .............. 604/533 |

(Continued)

FOREIGN PATENT DOCUMENTS

EP  0 715 864  6/1996
EP  0 947 213  10/1999

OTHER PUBLICATIONS

International Search Report for PCT/IT2005/000098 dated May 24, 2005.

*Primary Examiner*—Nicholas D Lucchesi
*Assistant Examiner*—Quynh-Nhu H Vu
(74) *Attorney, Agent, or Firm*—Nixon & Vanderhye P.C.

(57) ABSTRACT

A device is described for fitting and removing a closing means (27, 29) on an end portion (13) of a tubular element (3), comprising: a container (1) defining an internal chamber (18); a rotating platform (19) inside said chamber at the bottom (16) thereof; a receiving housing (26) that is able to receive and hold a first closing means (27) from said end portion of tubular element; and a releasing housing (28) that is able to contain and release a second closing means (29), in said end portion of tubular element; said receiving and releasing housings provided with an opening for passage of the closing means, being fixed on said rotating platform with said opening turned towards said perimeter walls (17) of the container. The device can be used as a connector for peritoneal dialysis and minimizes or eliminates the risks of contamination, also of pathogens, and the risks of peritonitis.

24 Claims, 7 Drawing Sheets

U.S. PATENT DOCUMENTS

| | | | |
|---|---|---|---|
| 4,821,996 A * | 4/1989 | Bellotti et al. | 251/9 |
| 4,950,230 A * | 8/1990 | Kendell | 604/28 |
| 5,221,267 A * | 6/1993 | Folden | 604/200 |
| 5,336,173 A * | 8/1994 | Folden | 604/29 |
| 5,533,983 A * | 7/1996 | Haining | 604/249 |
| 5,613,511 A * | 3/1997 | Andersen et al. | 134/167 R |
| 5,693,021 A * | 12/1997 | Diaz et al. | 604/187 |
| 5,694,978 A | 12/1997 | Heilmann et al. | |
| 5,713,850 A * | 2/1998 | Heilmann et al. | 604/28 |
| 5,785,693 A * | 7/1998 | Haining | 604/249 |
| 6,273,134 B1 * | 8/2001 | Edwards et al. | 137/625.46 |
| 6,482,189 B2 | 11/2002 | Döpper et al. | |
| 6,485,483 B1 | 11/2002 | Fujii | |
| 2004/0031756 A1 * | 2/2004 | Suzuki et al. | 210/646 |

\* cited by examiner

APPARATUS FOR APPLYING AND REMOVING CLOSING MEANS FROM AN END PORTION OF A TUBULAR ELEMENT AND THE USE THEREOF IN PERITONEAL DIALYSIS

This application is the US national phase of international application PCT/IT2005/000098 filed 23 Feb. 2005, which designated the U.S. and claims priority to IT PE2004A000004 filed 27 Feb. 2004, and IT PE2004A000016 filed 11 Aug. 2004, the entire content of each of which is hereby incorporated by reference.

The present invention relates to those fields where it is necessary to perform operations of opening and closing of tubular elements in conditions of controlled contamination, for example the health field, in particular the nephrolog. field, or the operations performed in clean rooms. More particularly the present invention aims to perfect the methodology of connection of a patient who is carrying out peritoneal dialysis.

BACKGROUND OF THE INVENTION

The main problem in peritoneal dialysis treatment is that of infections: their frequent consequences are hospitalization, "wearing out" of the peritoneal membrane owing to sepsis and cessation (drop-out) of the methodology.

To date, moreover, there is still no perfect "anticontamination" device: the German company Fresenius Medical Care has introduced a disposable peritoneal exchange device but this leaves open a window of potential infective contamination for approx. 50% of the total risk relative to exchange in manual ambulatory peritoneal dialysis (CAPD).

As the lines in which the dialysis solution flows are sterile and disposable, this risk is connected with the two moments of connection and disconnection of said lines.

Among the various solutions proposed by the manufacturers of equipment for peritoneal dialysis, mention is made of the company Fresenius Medical Care, which has attempted to eliminate the risk of contamination during connection, by devising a closing means, called "pin" here (a kind of sealing plug with O-ring seal), which a disposable cylindrical device with an operating handle pushes inside the lumen of the peritoneal catheter at the end of the peritoneal dialysis cycle. As this takes place with the catheter connected to the device, on disconnection of the peritoneal catheter from the device it is not possible for bacteria, viruses and other contaminating material to get into the catheter. However, before beginning the next cycle it is necessary to extract the used pin from the end of the catheter, before connecting to a new disposable device equipped with a new end-of-cycle pin. This extraction is carried out with suitable plugs with retaining clips which, screwed onto the end of the catheter, hook the used pin and, once unscrewed, extract it. This operation, performed in the open air by the patient's hands, again exposes him to the risk of contamination, and the more serious risk of peritonitis.

Another device is described in U.S. Pat. No. 6,485,483. Other devices for peritoneal dialysis which tackle the problem of contamination are described in U.S. Pat. No. 5,221,267, DE 10042067, U.S. Pat. No. 5,336,173, EP 0 092 528, U.S. Pat. No. 4,950,230 and GB 2 134 202.

The present invention sets itself the aim of completely or substantially eliminating the risk of peritonitis.

Because the choice of the methodology is still subordinated to pressing social conditions, for a patient of low socio-economic level (deficient hygiene, scant domiciliary area for providing a "controlled contamination" zone, insufficient cultural level or conditions of poor vigilance connected with age) this methodology will easily be proscribed, for reasons not primarily connected with the patient's condition, but relating to the safety of the methodology.

The aim ought to be achieved in the device rather than on the patient: since peritoneal dialysis is a health methodology for problems that are statistically more frequent in the third and fourth age, thus at times when the patient's compliance—both physical and mental—is often poor, we ought to prescind from considering the patient's contribution when planning the objectives of sterility, simplicity of use and safety. All of the objectives ought to be achieved by the device itself.

Therefore it is still felt that there is a great need for a connector for manual ambulatory peritoneal dialysis that would ensure sterility in the operations of manipulation of the dialysis device, that is both easy to use, especially for patients with poor dexterity and/or low level of training in hygiene and that would not require the assistance of specialized personnel.

SUMMARY OF THE INVENTION

A device that can be used as a connector for manual ambulatory peritoneal dialysis (CAPD), and solves the problems of the prior art, has now been found, and is the object of the present invention.

In its more general application, the present invention provides a device for fitting and removing a closing means on an end portion of a tubular element.

The device according to the present invention is characterized by a closing, preferably sealing, means, which is moved into the device so that it does not come in contact with the surroundings and the characteristics of sterility are maintained.

Owing to its characteristics, the device according to the present invention provides connection between the distal end of the peritoneal catheter and the peritoneal exchange bag or bags in a protected environment, not communicating with the exterior, making it impossible for bacteria, fungi, viruses and any other contaminating material to contaminate the end or the interior of the peritoneal catheter or the interior of the peritoneal exchange device.

Owing to its design characteristics, the way the device according to the present invention works can be understood easily and intuitively by the patient, so that it is practically possible to dispense with training by technical personnel. Particularly advantageously, the device can also be used by the blind, using appropriate indications on the device itself.

The device of the present invention can also offer functions that make it "error-proof" (for example mechanical locking devices for each operating position, one-way progression of the cycle phases, mechanical blocking of accidental disconnection).

Yet another advantage is that the cost of the disposable device is entirely compatible with the present costs borne by patients undergoing peritoneal dialysis.

Owing to the characteristics that will be described hereunder, the device according to the present invention practically cancels the contra-indications to the peritoneal dialysis technique connected with social-environmental problems and overcomes the limits for enrollment of candidate patients for peritoneal dialysis displaying physical, mental or social handicaps.

Therefore the device as defined in claim 1 and the claims dependent thereon is an object of the present invention.

Another object of the present invention is a method for fitting and removing a closing means on an end portion of a tubular element.

A further object of the present invention is the use of the device in peritoneal dialysis.

Yet another object of the present invention is a peritoneal catheter coupled to said device and the respective system for carrying out peritoneal dialysis.

Yet another object of the present invention is a method of carrying out peritoneal dialysis in a patient which does not require him to understand the system mentioned above.

One embodiment of the present invention will now be described in detail, referring to the appended drawings.

DETAILED DESCRIPTION OF THE INVENTION

Figure 1:
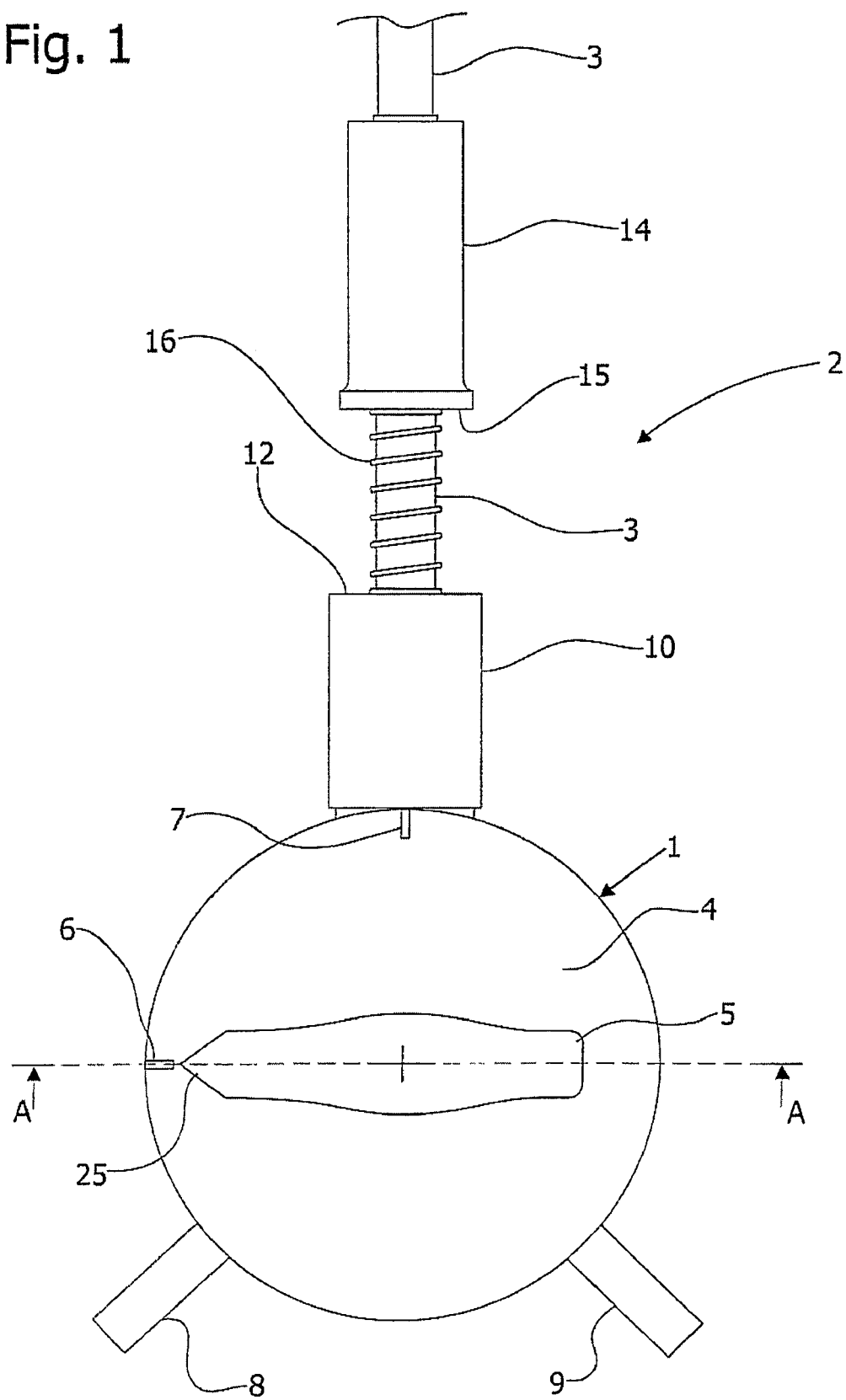
FIG. 1 is an overall top view of the device according to the present invention in a preferred embodiment thereof for use as connector for peritoneal dialysis.

Referring to the drawings, in particular to FIG. 1, this shows an overall top view of one embodiment of the device for fitting and removing a closing means on an end portion of a tubular element according to the present invention.

It comprises a container 1 and a connector 2 for putting container 1 in fluid communication with a tubular element 3.

Container 1 is provided with a cover 4, on which a rotating actuator in the form of a handle 5 is mounted. The cover also has two reference marks 6 and 7, whose function will become clear later. Container 2 can have fluid communication with other tubular elements (not shown), for example two in number, via two lines 8, 9 present on its perimeter wall.

Connector 2 comprises a sleeve 10, to be fitted to a connection 11 of container 1, shown in FIGS. 3 to 7, which are cross-sections of the device. Sleeve 10 is closed distally (relative to container 1) by a wall 12, through which the end portion 13 of tubular element 3—visible in FIGS. 3-7—passes. Tubular element 3 has an integral handgrip 14, having a proximal end stop 15 (relative to container 1), which encircles tubular element 3. A helical spring 16 is mounted between the distal wall 12 of sleeve 10 and the proximal end stop 15 of handgrip 14.

Figure 2:
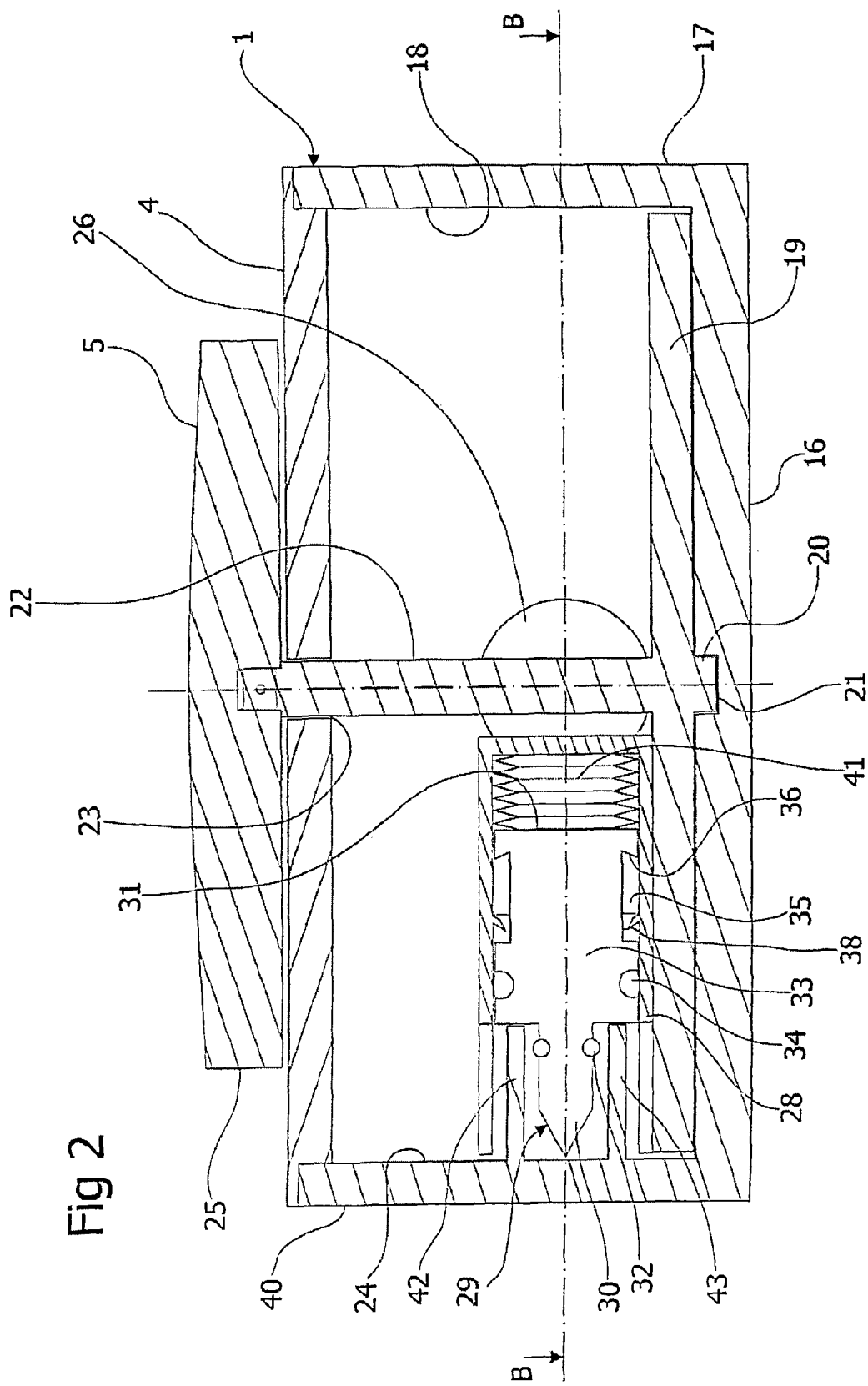
FIG. 2 is a magnified cross-section through a plane A-A of the device of FIG. 1.

Referring to FIG. 2, which is a substantially longitudinal section, through a plane A-A of the device of FIG. 1, this shows the interior of container 1. Container 1, substantially hollow, has a bottom 16 and a perimeter wall 17, which delimit, together with cover 4, a cylindrical internal chamber 18. A rotating platform 19 is mounted inside cylindrical chamber 18, preferably near the bottom 16. For convenience of manufacture it is advantageous for container 1 to be cylindrical, like the rotating platform 19, but other shapes are not excluded, even for the same internal chamber 18.

Platform 19 has centrally, beneath its base, a boss 20, which fits in a blind hole 21 correspondingly made on the inside of bottom 16 of the container. The platform 19 has an integral pin 22 projecting from cover 4 of container 1 via a through-hole 23 made in it. Handle 5 is fixed to pin 22, so that by manual action on the handle, the platform 19 can be rotated relative to the internal lateral surface of the container, which is indicated by 24. Owing to problems of assembly during manufacture, handle 5 is connected to pin 22 projecting from the cover by means of threaded coupling of the parts, then locked definitively with a pin. Naturally, alternative forms of fixing can be provided, by local fusion or gluing of pin 22 to handle 5, if, as is advisable, the materials of which these parts are constituted are plastics.

One end of handle 5 comes to a point 25, which serves to indicate the position of the rotating platform, in particular of certain components of the device mounted rigidly thereon.

Referring also to FIGS. 3, 4, 5, 6 and 7, said components mounted rigidly on rotating platform 19 comprise a receiving housing 26 that is able to receive and hold a first closing means 27 extracted from the end portion 13 of tubular element 3; and a releasing housing 28 that is able to contain and release a second closing means 29 in the end portion 13 of tubular element 3, after the first closing means 27 has been extracted. The receiving and releasing housings 26, 28 are positioned radially on the platform, and have an opening for passage of the closing means turned towards the internal lateral surface 24 of container 1. In the embodiment described, the housings have longitudinal axes, which are also orthogonal to the external lateral surface, indicated by 40. For reasons of clarity, the closing means 27, 29 are not sectioned in the drawings.

The closing means 27, 29 can be identical and comprise a pointed end 30 which is intended to be received in the end portion 13 of tubular element 3 and a tail end 31 opposite the pointed end.

The pointed end 30, suitably tapered, has an ogival shape for being inserted in the end portion of cylindrical tubular elements, although other shapes of tube section and hence of pointed end are not excluded.

A first circumferential groove for an O-ring 32 is provided in the pointed end 30 to create a fluid seal in the connection to tubular element 3.

The closing means 27, 29 preferably has a substantially cylindrical body 33, though it can have other shapes. A second circumferential groove for an O-ring 34 is provided on the cylindrical body 33. Moreover, still on the lateral surface of the cylindrical body 33, there is a peripheral recess 35, preferably terminating in an undercut 36 near the tail end 31. The functions of the individual parts will become clear from the rest of the description.

Figure 3:
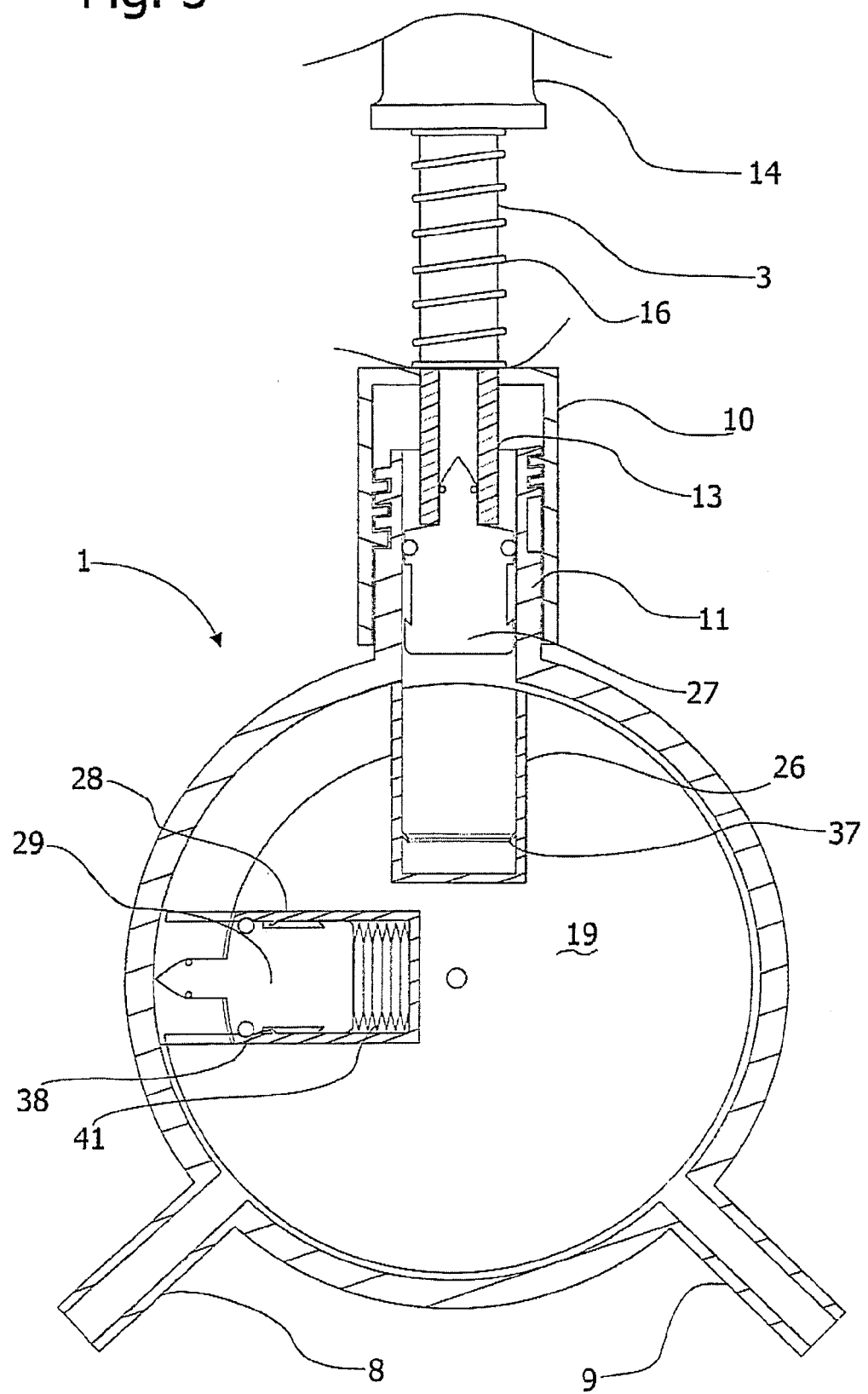
FIGS. 3, 4, 5, 6 and 7 are reduced-scale partial sections with parts removed, through a plane B-B of the device of FIG. 2, respectively in an arrangement shown in FIG. 2 and in four arrangements relating to four different moments during its use.

Referring to FIG. 3, which is a cross-section of the embodiment of the device according to the present invention, this shows the device with the platform 19 in a position corresponding to that shown in FIG. 2.

Accordingly, the disposition of the releasing housing 28 is such that its longitudinal axis is parallel to the major axis of handle 5 and is located, on the quadrant represented by cover 4, in the position of the reference mark 6. The disposition of the receiving housing 26 is such that its longitudinal axis is perpendicular to the major axis of handle 5 and is located, on the quadrant represented by cover 4, in the position of the reference mark 7.

It should be understood that the arrangement of orthogonality described above is not binding, and that the axes of the two housings 26, 28 could form between them an angle other than a right angle. The only thing that is important is that anyone looking at the container from the outside can see when one or other housing 26, 28 of the closing means is coaxial with the end portion 13 of tubular element 3, in such a way that the pointed end 30 of the closing means 27, 29 is also coaxial therewith.

Examining in detail the receiving and releasing housings 26, 28, it can be seen that they are different from one another, even though both have a shape corresponding to that of the closing means. The receiving housing 26 has internally, near its bottom, retaining means in the form of a preferably circumferential fin 37 projecting inside the receiving housing 26 and inclined towards the bottom thereof. When the closing means 27 is received inside the receiving housing 26, as will be seen later, the circumferential fin 37 is intended to be inserted in the peripheral recess 35 of the closing means 27 and to engage with the undercut 36 of the latter.

In contrast, the releasing housing 28, seen better in FIG. 2, has internally, in a substantially central position, stopping means in the form of a preferably circumferential fin 38 projecting inside the releasing housing 28 and inclined towards the opening thereof, i.e. towards the lateral surface 24 of cylindrical chamber 18 of container 1. When the closing means 29 is released from the inside of the releasing housing 28, as will be seen later, the circumferential fin 38 is intended to bend towards the inside surface of the housing and cause the closing means 29 to come out, preventing it from re-entering the releasing housing 28.

To be able to come out of the releasing housing 28, the closing means 29 contained inside receives a thrust from an elastic component previously positioned between the tail end 31 of the closing means 29 and the bottom (not assigned a reference number) of the housing. The elastic component has been represented as a multiple-plate spring 41, which can also be made easily in plastics. Plate spring 41 is able to cause the closing means 29 to travel a predetermined distance towards connection 11, obviously when the closing means is next to the latter.

In the arrangement of FIG. 2, the releasing housing 28 of the closing means 29 is located on platform 19 next to the reference mark 6. For this reason, the thrust exerted by plate spring 41 would lead the pointed end 30 of the closing means 29 to come up against the internal lateral surface 24 of container 1. To prevent probable twisting of the pointed end 30, during rotation of the platform for bringing closing means 9 next to connection 11 for its release on the end portion 13 of tubular element 3, the front part of the body 33 of the closing means 29 is caused to strike a pair of parallel fixed cams, upper and lower, with a circumferential arc, indicated by 42 and 43 respectively.

The circumferential-arc fixed cams 42, 43 are not present next to the opening of connection 11 so as to permit exit of the closing means under the action of plate spring 41.

As shown in FIGS. 3 to 7, the coupling of connector 2 to container 1 is of the threaded type, with an internal thread 44 on sleeve 10 and a corresponding external thread 45 on connection 11 projecting towards the outside of the lateral external surface 40 of container 1.

Obviously other forms of coupling may come to mind to a person skilled in the art, also depending on the various applications of the device according to the invention.

The functioning of the device is as follows.

Figure 4:
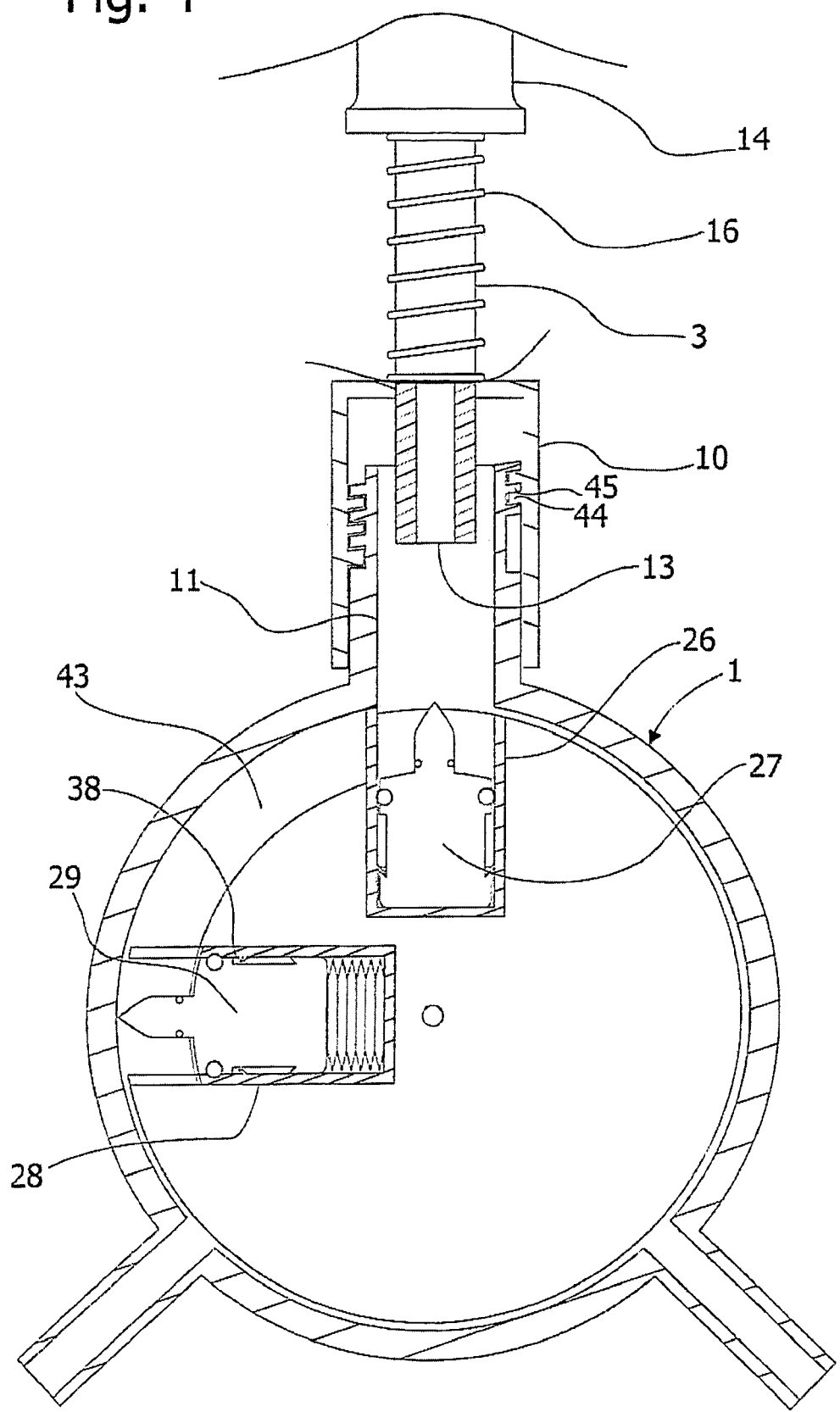

When it is necessary to replace a closing means with an end portion 13 of a tubular element 3, the device of the invention is provided with a single closing means inside, that indicated with 29 in the releasing housing 28 in the position indicated by the reference mark 6 on cover 4 of the container. It is then applied to tubular element 3 provided with its closing means 27 in its end portion 13, by screwing down sleeve 10 of the connector on connection 11 (FIG. 3). By acting on handgrip 14 against the action of spring 16, the end portion 13 of the tubular element is caused to advance inside connection 11 until it brings the closing means 27 to the bottom of the receiving housing 26 (FIG. 4). Part of the body 33 of the closing means 27 has thus overcome the retaining fins 37, which project elastically towards the inside of the housing and engage with the undercuts 36, retaining them. Rotating handle 5, less than 90° clockwise, the receiving housing 26 can be moved to free the opening of connection 11, for all the necessary operations. If the housing 26 is a cylinder closed on all sides, except for the opening, the opening will now also be closed by side wall 17 of container 1.

Figure 5:
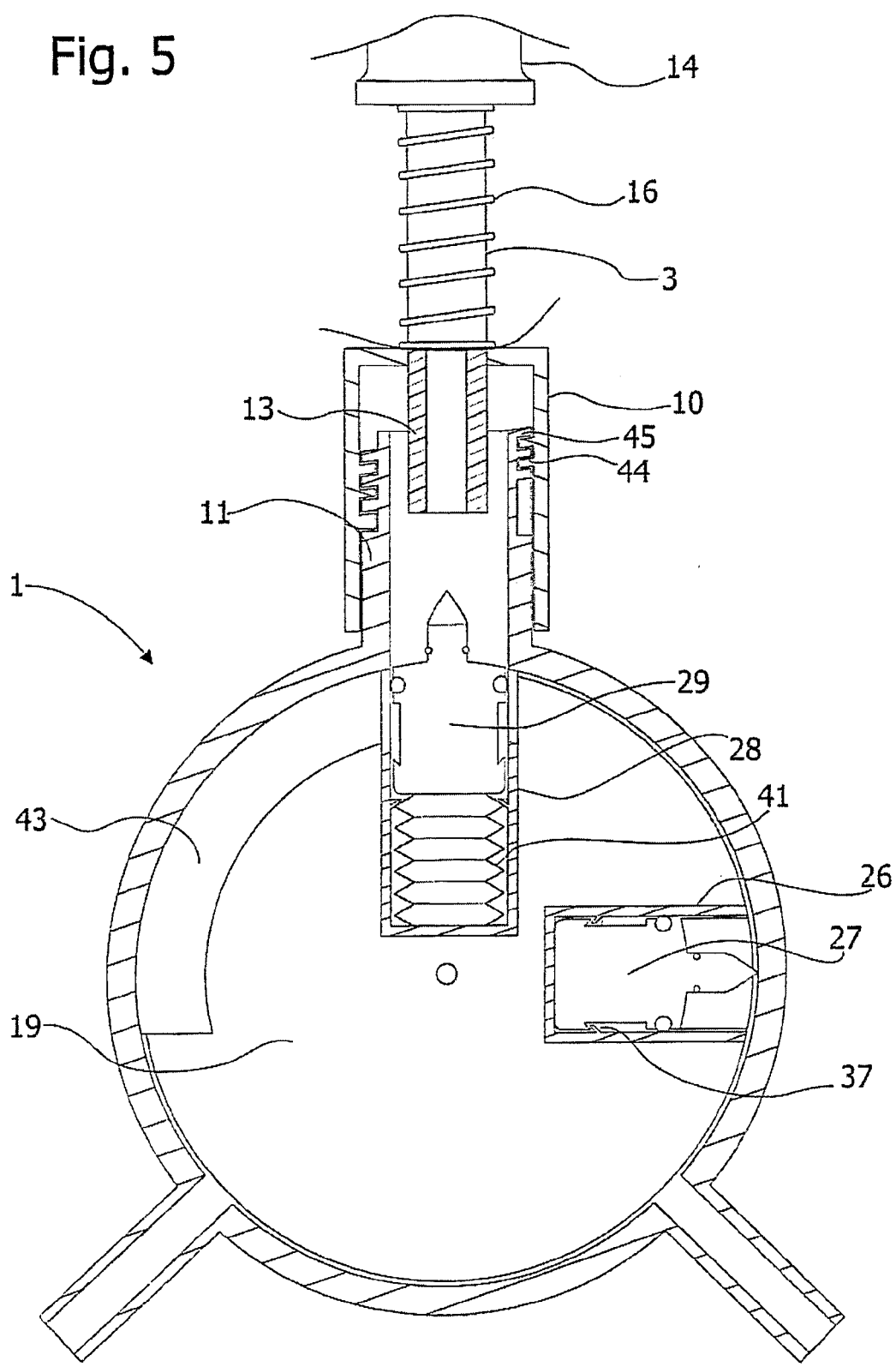

When a new closing means has to be applied on the end portion 13 of tubular element 3, handle 5 is rotated clockwise until its point 25 coincides with the reference mark 7. Thus, the releasing housing 28 of the closing means 29 on the platform 19 is brought next to the opening of connection 11. FIG. 5 shows the closing means 29 after being made to advance by plate spring 41, no longer blocked by the fixed cams 42, 43. It can be seen that in its approach to the end portion 13 of tubular element 3, the body 33 passed over the stopping fins 38, which now oppose the return travel of the closing means 29.

Figure 6:
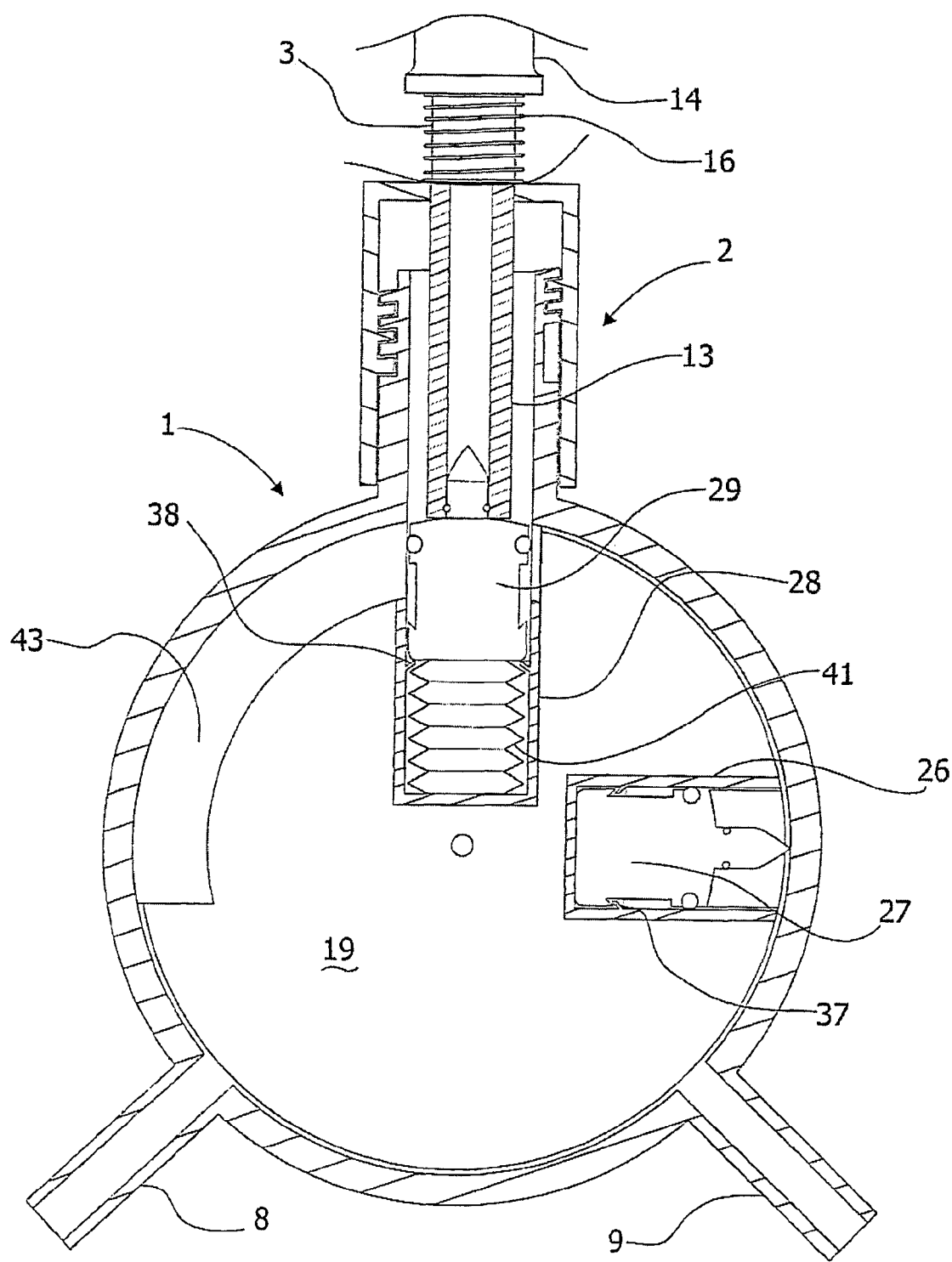
Figure 7:
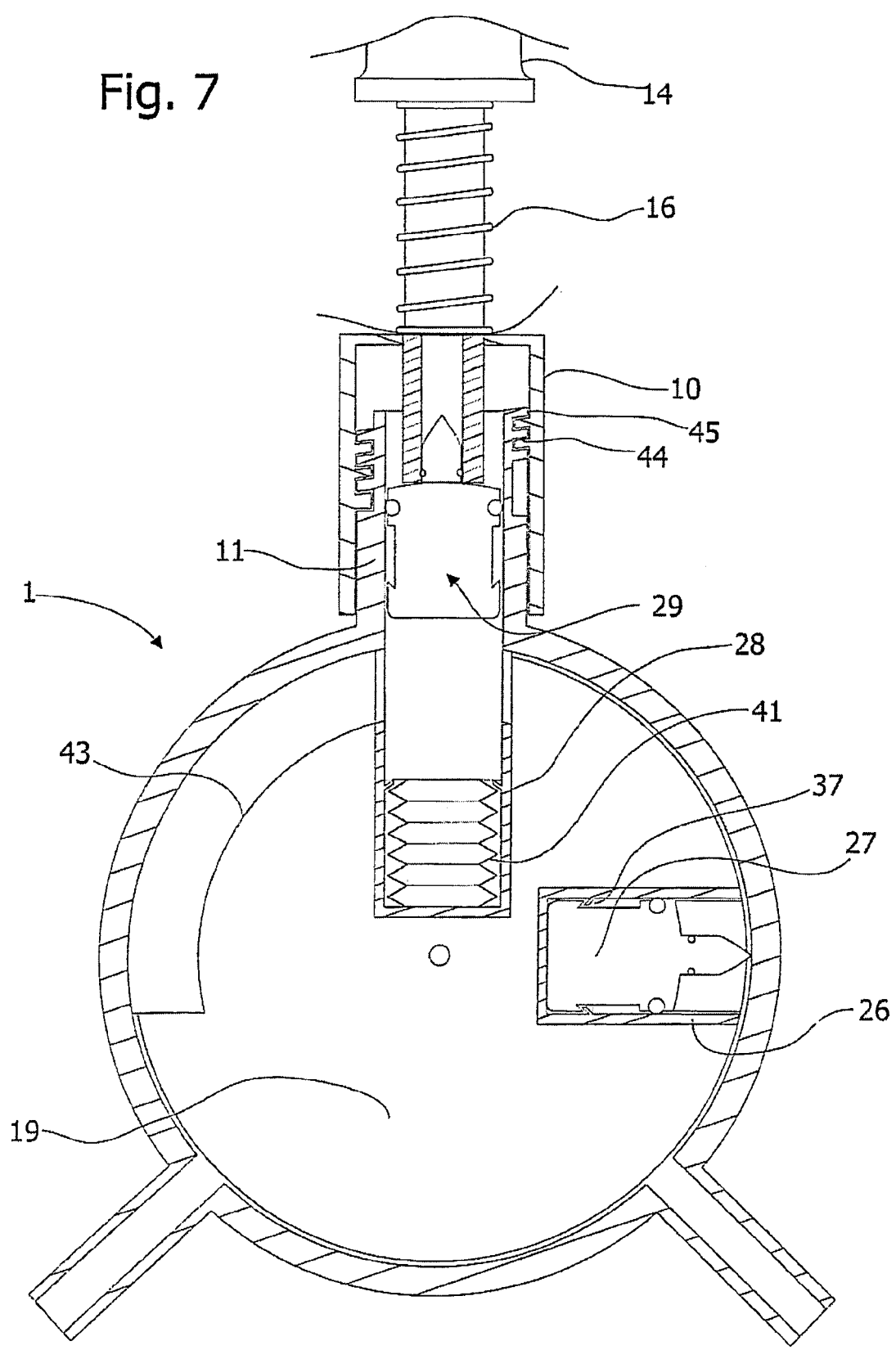

As shown in FIG. 6, by acting on charging handgrip 14 of spring 16, the end portion 13 of tubular element 3 is brought closer until it encircles the pointed end 30 of the closing means 29. The O-ring seal enables tubular element 3 to remain engaged with the closing means 29, utilizing the contrast with the stopping fin 38. At this point it is sufficient for the user to release the force applied on handgrip 14, because spring 16 withdraws, into sleeve 10, the end portion 13 closed with the closing means 29. All that remains is to unscrew connector 2 from container 1, to complete the operation of replacement of the closing means 27 with the new closing means 29.

A preferred embodiment of the device according to the present invention envisages its use in the construction of a connector for fluid exchange in a peritoneal dialysis system, in particular in a CAPD system. In said embodiment, the end portion 13 of a tubular element 3 envisaged in the general description of the invention, is the distal end of a peritoneal catheter. In this case, it is desirable to replace the closing means 27 of catheter 3, which comes from the preceding dialysis cycle and is therefore potentially contaminated, with the new closing means 29 contained in the device and intended to close catheter 3 at the end of the dialysis cycle so as to ensure non-contamination of the system.

There are many ways of accomplishing the coupling between connection 11 and connector 2, easily carried out by a person skilled in the art. It may be preferable to use a coupling of the threaded type 44-45 as described above. In the case when the device according to the present invention is used as connector for peritoneal dialysis, those types of connector normally employed in the medical devices field can be used, for example as described in the documents of the prior art mentioned above. One of the preferred types of coupling is that known as luer lock.

To improve the hermeticity of the system and in particular the characteristics of non-contamination, in the device according to the present invention the receiving housing is a receptacle that is open on the side facing the perimeter walls, and is liquid-tight against them.

It is appropriate to provide, at the pointed end 30 of the closing means 27, 29, sealing means that interact with the end portion 13 of tubular element 3. Once again, a person skilled in the art will have no difficulty in envisaging suitable sealing means, also differing from the O-rings stated above.

In a preferred embodiment of the present invention, the pointed end 30 of the closing means 27, 29 extends towards the tail end 31 thereof with a body of diameter greater than the diameter of tubular element 3.

The device according to the present invention is suitable for manual use or it can be included in automatic switching systems. In the last-mentioned case, the actuator will be different from handle 5 and will be connected to the automatic system.

To make it easier to use, and minimize the possibility of error, especially in the case of patients undergoing peritoneal dialysis, cover 4 has the reference marks 6, 7, externally, for the handle for positioning the former and the releasing housing.

In the preferred embodiment of the present invention, container 1 further includes lines 7, 8 as two routes of communication with the exterior 7, 8. Conveniently, the two routes of communication are connections for end portions of tubular elements different from tubular element 3.

In an even more preferred embodiment, the device according to the present invention, especially for use as connector for peritoneal dialysis, is provided with valved means for selectively establishing the passage of a fluid between connection 11 for coupling to tubular element 3 and one of said two routes of communication at a time. Such means are known in this field and are described for example in the patents cited above. For example, a cam system, as used in the Fresenius devices, may be suitable for this purpose.

In the applications that call for absence of contamination, such as medical and health applications, or any operation requiring absence of external contamination, the receiving housing 26, and if necessary also the releasing housing 28 contain disinfecting means, for example povidone gel.

To ensure compliance with good rules of hygiene, connection 11 is cloed in a suitable way, for example with a fracture membrane.

Conveniently, tubular element 3 has, at its distal end, means for coupling to connection 11 of the device.

In a particularly preferred embodiment of the invention, tubular element 3 described above forms part of a catheter for peritoneal dialysis.

Means can be provided on the catheter for visual indication of the number of cycles of peritoneal dialysis.

Another object of the present invention is a set for peritoneal dialysis comprising the device and the catheter described here.

The present invention also comprises a method for removing and fitting a closing means 27, 29 to an end portion 13 of a tubular element 3, comprising the steps of:

a) coupling the end portion 13 provided with a first closing means 27 to connection 11 of the device according to the present invention;
b) passing the end portion 13 through said connection 11 until the first closing means 27 engages with a receiving housing 26 that is able to receive and hold said closing means 27;
c) retracting said end portion 13 releasing said closing means 27;
d) acting on the actuator so as to cause the rotating platform 19 to rotate and move away said receiving housing 26 and bring up a releasing housing 28 that is able to contain and release a second closing means 29,
e) passing the end portion 13 through connection 11 until it engages with said second closing means 29 contained in said releasing housing 28;
f) retracting said end portion 13 provided with said closing means 29.

A further object of the present invention is a method of using the device described here as connector for peritoneal dialysis, in particular in a subject undergoing peritoneal dialysis, said method comprising:

a) coupling a peritoneal catheter 3 provided at its distal end with a first closing means 27 to connection 11 of said device;
b) coupling a second line 8 to a source of peritoneal dialysis solution;
c) coupling a third line 9 to a drainage system;
d) passing said distal end 13 through said connection 11 until said first closing means 27 engages with a receiving housing 26 that is able to receive and hold said closing means 27;
e) retracting said distal end 13, releasing said closing means 27;
f) acting on actuator 5 so as to rotate the rotating platform 19 and move away said receiving housing 27 and allow the peritoneal dialysis solution to pass through said first line 8 to catheter 3, thus carrying out the dialysis treatment;
g) acting on actuator 5 so as to rotate the rotating platform 18 and allow the peritoneal dialysis solution to pass through said third line 9 to the drainage system;
h) acting on actuator 5 so as to rotate the rotating platform 18 and bring up a releasing housing 28 that is able to contain and release a second closing means 29 for said distal end 13;
i) passing said distal end 13 through said connection 11 until it engages with said second closing means 29 contained in said releasing housing 28;
j) retracting said distal end 13 provided with said closing means 29.

The set for peritoneal dialysis comprises a portion pertaining to the peritoneal catheter and a portion pertaining to the solution bag and the drainage bag.

There now follows a description of a particularly preferred embodiment of the present invention, envisaging the use of the device described here in its use as connector for peritoneal dialysis together with the catheter coupled to said connector.

The portion pertaining to the peritoneal catheter is configured as a particular series (lasting six months or more, depending on the material used in manufacture), at the distal end of which there is a charging handgrip 14 (mandrel) shaped for the fingers; at the end of the mandrel there is a system for locking to the exchange device, by means of a luer-lock coupling which confirms completion of screwing with a "click".

The device according to the present invention is coupled by means of the dedicated connectors to the source of solution for peritoneal dialysis, for example a bag, and to the drainage, for example a suitable bag.

Then the mandrel, which encircles the peritoneal catheter closed by its closing means, is connected to the exchange device, which is the disposable portion of the device and is constituted of the solution and drainage bags and the flow distributor or valved means.

By means of actuator 5, the receiving housing 26 is positioned next to connection 13 for coupling between the internal chamber 18 of the device and the peritoneal catheter 3.

Once connected to the exchange device, the mandrel 14, pushed by the fingers of the patient who is being connected, causes the end 13 of catheter 3 to slide forward, so as to cause it to pass through the coupling connection 11.

This movement positions the closing means 27 of catheter 3, inserted at the end of the preceding dialysis cycle, in the receiving housing 26, which holds it by means of the retaining means 37 which engage with the respective portions of the undercut 36 present in the received closing means 27. Advantageously, the closing means 27 incorporates seals, for example O-ring 34, which provide a sealed joint with the housing. This sealing also seals any contaminants inside the housing 26.

In fact, the end of travel of the end of catheter 3, reached with the pressure of the fingers, couples the used closing means 27 to the respective housing 26 and seals it definitively.

The travel can be determined manually from perception of attainment of engagement of the retaining means 37 by the closing means 27, or the elastic component 16 in abutment on the mandrel (which can be of plastic or metal, helical or unconventional) can be designed so as to ensure appropriate travel of the mandrel until the closing means 27 is held by its housing 26. Advantageously, on cessation of the force of the fingers pushing catheter 3 constrained by the mandrel against the device, the spring pulls back the end of catheter 3.

The catheter is completely protected from contamination. The housing 26 for receiving and holding the used closing means 27 can be filled with a disinfectant, for example sponge with povidone gel. This gel wets the outside of the catheter which is still closed by the used closing means on insertion into the device, reducing the bacterial load of the outside of the catheter, as a further, additional safety system.

At this point, the rotating platform 19 can be made to rotate by means of the actuator, which in the case of manual operation is controlled by handle 5 from the outside of container 1, and move away the receiving housing 26 and execute the dialysis treatment. At the end of the dialysis cycle, action on the actuator causes the rotating platform 19 to rotate and carry the releasing housing 28 which contains the second closing means 29 which will close catheter 3 next to connection 11 for coupling to the catheter.

Repeating the operation with the mandrel, this time the distal end is passed through connection 11 until it engages the new closing means 29 contained in its housing 28; the closed catheter is retracted.

As a further useful feature of the catheter-device system, the catheter has visual signals, to indicate the correct number of cycles of extraction of the closing means (dialysis cycles), and hence the need to replace the system. For example, it is possible to provide a drum coaxial with the translation axis of the catheter inside the mandrel which, rotating about its axis driven by a protuberance of the catheter, with speed reduction by a small gear train, activates the visual signals.

The invention claimed is:

1. A connector device for fitting and removing a closing means on an end portion of a tubular element, comprising:
   a) a container provided with a cover; said container having a bottom and perimeter walls extending from said bottom to said cover, so as to define an external lateral surface of the container and the lateral surface of an internal chamber of said container;
   b) at least one connection extending from said external lateral surface of the container for coupling said internal chamber to a tubular element of specified diameter the connection being engaged with a connector comprising a sleeve coupled to said connection, said connector comprising a spring abutting between said sleeve and a charging handgrip;
   c) a rotating platform inside said chamber at the bottom thereof;
   d) a pin integral with said rotating platform;
   e) an actuator for rotation of said pin;
   f) at least one closing means, having a pointed end intended to be received in said end portion of the tubular element and a tail end opposite to the pointed end; and
   g) a receiving housing that receives and holds a first closing means from said end portion of the tubular element; and a releasing housing that contains and releases a second closing means, in said end portion of the tubular element; said receiving and releasing housings within said container, provided with an opening for passage of the closing means, being fixed on said rotating platform with said opening turned towards said perimeter walls;
   wherein said charging handgrip, said sleeve and said spring being arranged so as to bring the end portion of the tubular element closer to one of said receiving and releasing housings.

2. The device as claimed in claim 1, characterized in that said receiving housing comprises, internally, retaining means, and said closing means has undercut portions which are able to receive said retaining means when said closing means is received in said receiving housing.

3. The device as claimed in claim 2, characterized in that said connection is passable for coupling of said end portion of tubular element with the pointed end of the first and of the second closing means.

4. The device as claimed in claim 1, characterized in that said closing means is held spring-loaded radially inside said releasing housing.

5. The device as claimed in claim 4, characterized in that the spring-loaded closing means is subjected to the action of an elastic component positioned inside said releasing housing capable of abutting against said tail end of the closing means to cause the closing means to travel a predetermined distance towards said connection.

6. The device as claimed in claim 5, characterized in that the perimeter walls of the container constitute a stop for said closing means under the action of the elastic component.

7. The device as claimed in claim 5, characterized in that the perimeter walls of the container have at least one pair of fixed cam elements for said closing means projecting circumferentially from the perimeter walls on one side relative to said connection.

8. The device as claimed in claim 4, characterized in that said releasing housing comprises stopping means, and said closing means has a peripheral recess able to receive said stopping means when said closing means is contained in said releasing housing; said stopping means being able to prevent the withdrawal of the closing means in the space of the predetermined travel of said elastic component.

9. The device as claimed in claim 1, characterized in that said coupling is of the threaded type.

10. The device as claimed in claim 9, characterized in that said coupling is of the luer lock type.

11. The device as claimed in claim 1, characterized in that said receiving housing is a receptacle that is open on the side facing the perimeter walls and is liquid-tight against them.

12. The device as claimed in claim 1, characterized in that said pointed end of the closing means comprises sealing means which interact with said end portion of tubular element.

13. The device as claimed in claim 1, characterized in that said pointed end of the closing means extends towards said tail end thereof with a body of diameter greater than the diameter of said tubular element.

14. The device as claimed in claim 1, characterized in that said actuator is constituted of a handle coupled to said pin passing through said cover.

15. The device as claimed in claim 14, characterized in that said cover has, externally, reference marks for the handle for positioning the receiving and releasing housings.

16. The device as claimed in claim 1, characterized in that said container further includes two routes of communication with the exterior.

17. The device as claimed in claim 16, characterized in that said two routes of communication are connections for end portions of tubular elements.

18. The device as claimed in claim 1, provided with valved means for selectively establishing the passage of a fluid between said connection for coupling to said tubular element and one of said two routes of communication at a time.

19. The device as claimed in claim 18, characterized in that said releasing housing contains disinfecting means.

20. The device as claimed in claim 18, characterized in that said disinfecting means are constituted of povidone gel.

21. The device as claimed in claim 1, characterized in that said receiving housing contains disinfecting means.

22. The device as claimed in claim 1, characterized in that said connection is closed with a fracture membrane.

23. A set for peritoneal dialysis, comprising a catheter and a connector device for fitting and removing a closing means on an end portion of the catheter, wherein the device comprises:
 a) a container provided with a cover and two routes of communication with the exterior; said container having a bottom and perimeter walls extending from said bottom to said cover, so as to define an external lateral surface of the container and the lateral surface of an internal chamber of said container;
 b) at least one connection extending from said external lateral surface of the container for coupling said internal chamber to the catheter; the connection being engaged with a connector comprising a sleeve coupled to said connection, said connector comprising a spring abutting between said sleeve and a charging handgrip;
 c) a rotating platform inside said chamber at the bottom thereof;
 d) a pin integral with said rotating platform;
 e) an actuator for rotation of said pin;
 f) at least one closing means, having a pointed end intended to be received in said end portion of the catheter and a tail end opposite to the pointed end; and
 g) a receiving housing that receives and holds a first closing means from said end portion of the catheter; and a releasing housing that contains and releases a second closing means, in said end portion of catheter; said receiving and releasing housings within said container, provided with an opening for passage of the closing means, being fixed on said rotating platform with said opening turned towards said perimeter walls;
wherein said charging handgrip, said sleeve and said spring being arranged so as to bring the end portion of the catheter closer to one of said receiving and releasing housings.

24. The set as claimed in claim 23, wherein the catheter has visual means of indication of the number of cycles of peritoneal dialysis.

\* \* \* \* \*